(12) United States Patent
Brill et al.

(10) Patent No.: US 10,994,136 B2
(45) Date of Patent: May 4, 2021

(54) SYSTEMS AND METHODS FOR DETERMINING NEUROMODULATION PARAMETERS

(71) Applicant: Boston Scientific Neuromodulation Corporation, Valencia, CA (US)

(72) Inventors: Natalie A. Brill, Valencia, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 66 days.

(21) Appl. No.: 16/267,034

(22) Filed: Feb. 4, 2019

(65) Prior Publication Data
US 2019/0247657 A1    Aug. 15, 2019

Related U.S. Application Data

(60) Provisional application No. 62/628,506, filed on Feb. 9, 2018.

(51) Int. Cl.
*A61N 1/36* (2006.01)
*A61N 1/04* (2006.01)

(52) U.S. Cl.
CPC ....... *A61N 1/36031* (2017.08); *A61N 1/0456* (2013.01); *A61N 1/0476* (2013.01);
(Continued)

(58) Field of Classification Search
CPC combination set(s) only.
See application file for complete search history.

(56) References Cited

U.S. PATENT DOCUMENTS 7,801,601 B2   9/2010   Maschino et al.
8,099,170 B2   1/2012   Jensen et al.
(Continued)

FOREIGN PATENT DOCUMENTS

| CN | 105848575 A | 8/2016 |
|---|---|---|
| EP | 3181192 A1 | 6/2017 |
| WO | WO-2019156936 A1 | 8/2019 |

OTHER PUBLICATIONS

"International Application Serial No. PCT/US2019/016530, International Preliminary Report on Patentability dated Aug. 20, 2020", 7 pgs.

(Continued)

*Primary Examiner* — Gary Jackson
*Assistant Examiner* — Zahed Kabir
(74) *Attorney, Agent, or Firm* — Schwegman Lundberg & Woessner, P.A.

(57) ABSTRACT

This document discusses, among other things, systems and methods for providing pain relief to a patient. Recording circuitry may receive electrical signals corresponding to evoked compound action potentials in the patient that may be produced in response to external stimulation of a location where the patient is experiencing pain. The received electrical signals may be stored in a memory. Internal stimulation may then be applied to the patient and control circuitry may receive electrical signals corresponding to evoked compound action potentials in the patient that may be produced in response to the internal stimulation. The control circuitry may then adjust electrical parameters of the internal stimulation, such as to reduce a difference between the electrical signals corresponding to evoked compound action potentials produced in response to the internal stimulation and electrical signals corresponding to evoked compound (Continued)

action potentials produced in response to the external stimulation.

20 Claims, 10 Drawing Sheets

(52) U.S. Cl.
CPC ....... *A61N 1/0488* (2013.01); *A61N 1/36139* (2013.01); *A61N 1/36014* (2013.01); *A61N 1/36021* (2013.01); *A61N 1/36062* (2017.08); *A61N 1/36071* (2013.01)

(56) References Cited

U.S. PATENT DOCUMENTS

| | | |
|---|---|---|
| 8,527,059 B2 | 9/2013 | Demulling et al. |
| 8,868,199 B2 | 10/2014 | Kaula et al. |
| 9,248,279 B2 | 2/2016 | Chen et al. |
| 9,314,627 B2 | 4/2016 | Arcot-Krishnamurthy et al. |
| 9,511,231 B1 | 12/2016 | Kent et al. |
| 9,586,053 B2 | 3/2017 | Moffitt et al. |
| 9,662,495 B2 | 5/2017 | Moffitt et al. |
| 2005/0246004 A1 | 11/2005 | Cameron et al. |
| 2007/0179557 A1* | 8/2007 | Maschino .......... A61N 1/36071 607/45 |
| 2008/0161894 A1* | 7/2008 | Ben-David ............ A61B 5/412 607/116 |
| 2014/0277282 A1 | 9/2014 | Jaax |
| 2015/0012064 A1* | 1/2015 | Chen ................... A61N 1/0551 607/59 |
| 2016/0001096 A1* | 1/2016 | Mishelevich ............ A61N 7/00 601/2 |
| 2016/0022995 A1 | 1/2016 | Kothandaraman et al. |
| 2016/0136443 A1 | 5/2016 | Grandhe et al. |
| 2016/0303376 A1* | 10/2016 | Dinsmoor ........... A61N 1/0551 |
| 2016/0339251 A1* | 11/2016 | Kent .................. A61B 5/04001 |
| 2016/0375248 A1 | 12/2016 | Carcieri et al. |
| 2017/0209702 A1 | 7/2017 | Lee |
| 2017/0361101 A1* | 12/2017 | Single .................. A61N 1/0551 |
| 2018/0078769 A1* | 3/2018 | Dinsmoor .......... A61N 1/36071 |

OTHER PUBLICATIONS

"International Application Serial No. PCT/US2019/016530, International Search Report dated May 14, 2019", 3 pgs.

"International Application Serial No. PCT/US2019/016530, Written Opinion dated May 14, 2019", 5 pgs.

* cited by examiner

SYSTEMS AND METHODS FOR DETERMINING NEUROMODULATION PARAMETERS

CLAIM OF PRIORITY

This application claims the benefit of priority under 35 U.S.C. § 119(e) of U.S. Provisional Patent Application Ser. No. 62/628,506, filed on Feb. 9, 2018, which is herein incorporated by reference in its entirety.

TECHNICAL FIELD

This document relates generally to medical devices, and more particularly, to systems, devices and methods for delivering neural modulation.

BACKGROUND

Neuromodulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulator, also referred to as an implantable pulse generator (IPG), and one or more implantable leads each including one or more electrodes. The implantable neuromodulator may deliver neuromodulation energy through one or more electrodes placed on or near a target site in the nervous system, and an external programming device may be used to program the implantable neuromodulator with stimulation parameters controlling the delivery of the neuromodulation energy.

Neuromodulation energy may be delivered using electrical energy that may have stimulation parameters to specify spatial (where to stimulate), temporal (when to stimulate) and/or informational (stimulation patterns directing the nervous system to respond as desired) aspects of a pattern of neuromodulation pulses.

SUMMARY

This document discusses, among other things, systems and methods to receive electrical signals from a first set of electrodes implanted within a patient, the first set of electrodes being configured to receive electrical signals representing evoked compound action potentials (ECAPS) generated by the patient in response to external stimulation of a location on the patient's body and record the received electrical signals in a memory, apply electrical signals to electrodes in a second set of electrodes implanted within the patient to provide neuromodulation to the patient, and receive electrical signals representing evoked compound action potentials received at the first set of electrodes, the evoked compound action potentials being generated by the patient in response to the electrical signals applied to electrodes in the second set of electrodes by the stimulation circuitry, and adjust electrical parameters of the applied electrical signals to the second set of electrodes until received electrical signals representing evoked compound action potentials at the first set of electrodes match the received electrical signals representing evoked compound action potentials stored in the memory corresponding to the first set of electrodes.

Several neural elements may be involved in pain neural networks, such as may be described in gate control theory of pain. The neural elements may include A beta fibers, inhibitory interneurons, and pain transmission fibers. External stimulation may be used to sense neural elements that may be engaged during activation of a dermatomal area of pain in a patient. During external stimulation, target ECAPs may be captured at several regions near neural elements of interest (e.g. superficial dorsal horn, dorsal columns, and dorsal roots). Stimulation parameters may be designed to target the neural elements that were active during external stimulation in order to improve therapeutic outcomes.

Spinal cord circuits (e.g., implantable electrodes and stimulation circuitry) may be used to increase or maximize the target ECAP recorded across several neural elements. For example, caudal electrodes near the dorsal horn may sense neural elements that activate in response to rostral dorsal column fibers near rostral electrodes at the midline. In such an approach, the dorsal horn region may be targeted directly by locating the region of importance based on the target ECAP recorded during external stimulation. The direct dorsal horn target that may be linked to the external painful dermatome may be activated with sub-perception parameters. In another example, electrodes placed laterally near the root fibers may sense the activation of dorsal column fibers connected to the external stimulation (e.g., at the dermatome of pain or dermatomes near the dermatome of pain), as well as the rostral midline electrodes near the dorsal column. Then stimulation may be initiated at the electrodes near the roots while sensing is done in electrodes near the mid-line rostral electrodes by dorsal columns. The stimulation may be adjusted to increase or maximize the similarity of the sensed ECAP at the rostral midline electrodes near the dorsal columns to the prior sensed ECAP when external stimulation was applied. Different regions may be stimulated simultaneously to augment network effects (e.g. surround inhibition), or in sequence to potentially prevent habituation.

An example (e.g., "Example 1") of subject matter (e.g., a system) may include recording circuitry configured to receive electrical signals from a first set of electrodes implanted within a patient, the first set of electrodes being configured to receive electrical signals representing evoked compound action potentials generated by the patient in response to external stimulation of a location on the patient's body and record the received electrical signals in a memory. The system may also include stimulation circuitry configured to apply electrical signals to electrodes in a second set of electrodes implanted within the patient to provide neuromodulation to the patient. The system may also include control circuitry configured to receive electrical signals representing evoked compound action potentials received at the first set of electrodes, the evoked compound action potentials being generated by the patient in response to the electrical signals applied to electrodes in the second set of electrodes by the stimulation circuitry, and adjust electrical parameters of the applied electrical signals to the second set of electrodes until received electrical signals representing evoked compound action potentials at the first set of electrodes match the received electrical signals representing evoked compound action potentials stored in the memory corresponding to the first set of electrodes.

In Example 2, the subject matter of Example 1 may optionally be configured such that the location on the patient's body is a dermatomal target and wherein the control circuitry is configured to adjust electrical parameters of the electrical signals applied to the second set of electrodes provide stimulation of the dermatomal target.

In Example 3, the subject matter of any one or more of Examples 1-2 may optionally be configured such that the second set of electrodes includes electrodes on a paddle lead configured to provide spinal cord stimulation.

In Example 4, the subject matter of any one or more of Examples 1-3 may optionally be configured such that the adjusted electrical parameters include at least one of an amplitude, pulse width, or frequency.

In Example 5, the subject matter of any one or more of Examples 1-4 may optionally be configured such that the first set of electrodes is located proximal to a dorsal root ganglia of the patient.

In Example 6, the subject matter of any one or more of Examples 1-5 may optionally be configured such that the first set of electrodes is located in a neural foramen or epidural space of the patient.

In Example 7, the subject matter of any one or more of Examples 1-6 may optionally be configured such that the control circuitry is configured to instruct the stimulation circuitry to maintain a charge delivered to the second set of electrodes to maintain measured electrical signals representing evoked compound action potentials at the first set of electrodes.

In Example 8, the subject matter of any one or more of Examples 1-7 may optionally be configured such that the control circuitry is configured to use a matched filter to determine when the received electrical signals representing evoked compound action potentials at the first set of electrodes match the received electrical signals representing evoked compound action potentials stored in the memory corresponding to the first set of electrodes.

In Example 9, the subject matter of any one or more of Examples 1-8 may optionally be configured such that the control circuitry is configured to use a neural network to determine when the received electrical signals representing evoked compound action potentials at the first set of electrodes match the received electrical signals representing evoked compound action potentials stored in the memory corresponding to the first set of electrodes.

In Example 10, the subject matter of any one or more of Examples 1-9 may optionally be configured such that the control circuitry is configured to form a feature parameter space including one or more features extracted from the recorded evoked compound action potentials.

In Example 11, the subject matter of any one or more of Examples 1-10 may optionally be configured such that the control circuitry is configured to use a feature set comparison to determine when the received electrical signals representing evoked compound action potentials at the first set of electrodes match the received electrical signals representing evoked compound action potentials stored in the memory corresponding to the first set of electrodes.

In Example 12, the subject matter of any one or more of Examples 1-11 may optionally be configured such that the one or more features may include one or more of an amplitude, delay, width, or metric associated with an evoked compound action potential.

In Example 13, the subject matter of any one or more of Examples 1-12 may optionally be configured such that the stimulation circuitry is configured to apply electrical signals to electrodes in the first set of electrodes implanted within the patient, the applied electrical signals corresponding to evoked compound action potentials recorded by the first set of electrodes.

In Example 14, the subject matter of any one or more of Examples 1-13 may optionally be configured such that wherein the electrical signals applied to the first set of electrodes may stimulate a first neural element of a pain neural network and the electrical signals applied to the second set of electrodes may stimulate a second neural element of a pain neural network.

In Example 15, the subject matter of any one or more of Examples 1-14 may optionally be configured such that a first neural element and the second neural element may include at least one of A beta fibers, inhibitory interneurons, or pain transmission fibers.

An example (e.g., "Example 16") of subject matter (e.g., a method) may include receiving electrical signals from a first location, the received electrical signals representing the first evoked compound action potential generated by the patient in response to the external stimulation. The method may also include storing the received electrical signals corresponding to the first evoked compound action potential in a memory. The method may also include internally stimulating a location within the patient's body to generate a second evoked compound action potential. The method may also include receiving electrical signals from the first location, the received electrical signals representing the second evoked compound action potential generated by the patient in response to the internal stimulation. The method may also include determining a difference between the received electrical signals representing the second evoked compound action potential to the stored electrical signals corresponding to the first evoked compound action potential. The method may also include adjusting at least one electrical parameter of the internal stimulation to reduce the determined difference between the received electrical signals representing the second evoked compound action potential and the stored electrical signals corresponding to the first evoked compound action potential.

In Example 17, the subject matter of Example 16 may optionally be configured such that externally stimulating a location on a patient's body to generate a first evoked compound action potential includes externally stimulating a dermatomal target and/or nearby dermatomes.

In Example 18, the subject matter of Example 16 may optionally include adjusting at least one electrical parameter of the internal stimulation to provide neuromodulation to the dermatomal target and/or nearby dermatomes.

In Example 19, the subject matter of Example 16 may optionally be configured such that internally stimulating a location within the patient's body includes using electrodes on a lead to provide spinal cord stimulation.

In Example 20, the subject matter of Example 16 may optionally be configured such that adjusting at least one electrical parameter of the internal stimulation includes adjusting at least one of an amplitude, pulse width, or frequency.

In Example 21, the subject matter of Example 16 may optionally be configured such that receiving electrical signals representing the first evoked compound action potential generated by the patient in response to the external stimulation includes receiving electrical signals corresponding to an evoked compound action potential sensed proximal to the dorsal root ganglia.

In Example 22, the subject matter of Example 16 may optionally be configured such that receiving electrical signals representing the first evoked compound action potential generated by the patient in response to the external stimulation includes receiving electrical signals corresponding to an evoked compound action potential sensed proximal to the neural foramen.

In Example 23, the subject matter of Example 16 may optionally include using a matched filter to determine a difference between the received electrical signals representing the second evoked compound action potential and the stored electrical signals corresponding to the first evoked compound action potential.

An example (e.g., "Example 24") of subject matter (e.g., a non-transitory machine-readable medium) may include instructions that when executed by a machine, cause the machine to externally stimulate a location on a patient's body to generate a first evoked compound action potential, receive electrical signals from a first location, the received electrical signals representing the first evoked compound action potential generated by the patient in response to the external stimulation, store the received electrical signals corresponding to the first evoked compound action potential in a memory, internally stimulate a location within the patient's body to generate a second evoked compound action potential, receive electrical signals from the first location, the received electrical signals representing the second evoked compound action potential generated by the patient in response to the internal stimulation, determine a difference between the received electrical signals representing the second evoked compound action potential to the stored electrical signals corresponding to the first evoked compound action potential, adjust at least one electrical parameter of the internal stimulation to reduce the determined difference between the received electrical signals representing the second evoked compound action potential and the stored electrical signals corresponding to the first evoked compound action potential.

In Example 25, the subject matter of Example 24 may optionally include instructions, which when executed by the machine, cause the machine to adjust at least one electrical parameter of the internal stimulation to provide neuromodulation to a dermatomal target stimulated by the external stimulation.

In Example 26, the subject matter of Example 25 may optionally be configured such that adjusting at least one electrical parameter of the internal stimulation includes adjusting at least one of an amplitude, pulse width, or frequency.

In Example 27, the subject matter of Example 24 may optionally include instructions, which when executed by the machine, cause the machine to use a matched filter to determine a difference between the received electrical signals representing the second evoked compound action potential and the stored electrical signals corresponding to the first evoked compound action potential.

An example (e.g., "Example 28") of subject matter (e.g., a system) may include recording circuitry configured to receive electrical signals from a first set of electrodes implanted within a patient, the first set of electrodes being configured to receive electrical signals representing evoked compound action potentials generated by the patient in response to external stimulation of a location on the patient's body and record the received electrical signals in a memory. The system may also include stimulation circuitry configured to apply electrical signals to electrodes in a second set of electrodes implanted within the patient to provide neuromodulation to the patient. The system may also include control circuitry configured to receive electrical signals representing evoked compound action potentials received at the first set of electrodes, the evoked compound action potentials being generated by the patient in response to the electrical signals applied to electrodes in the second set of electrodes by the stimulation circuitry, and adjust electrical parameters of the applied electrical signals to the second set of electrodes until received electrical signals representing evoked compound action potentials at the first set of electrodes match the received electrical signals representing evoked compound action potentials stored in the memory corresponding to the first set of electrodes.

In Example 29, the subject matter of Example 28 may optionally be configured such that the location on the patient's body is a dermatomal target and wherein the control circuitry is configured to adjust electrical parameters of the electrical signals applied to the second set of electrodes provide stimulation of the dermatomal target.

In Example 30, the subject matter of Example 28 may optionally be configured such that the second set of electrodes includes electrodes on a paddle lead configured to provide spinal cord stimulation.

In Example 31, the subject matter of Example 28 may optionally be configured such that the adjusted electrical parameters include at least one of an amplitude, pulse width, or frequency.

In Example 32, the subject matter of Example 28 may optionally be configured such that the first set of electrodes is located proximal to a dorsal root ganglia of the patient.

In Example 33, the subject matter of Example 28 may optionally be configured such that the first set of electrodes is located in a neural foramen or epidural space of the patient.

In Example 34, the subject matter of Example 28 may optionally include control circuitry configured to instruct the stimulation circuitry to maintain a charge delivered to the second set of electrodes to maintain measured electrical signals representing evoked compound action potentials at the first set of electrodes.

In Example 35, the subject matter of Example 28 may optionally include control circuitry that may be configured to use a matched filter to determine when the received electrical signals representing evoked compound action potentials at the first set of electrodes match the received electrical signals representing evoked compound action potentials stored in the memory corresponding to the first set of electrodes.

In Example 36, the subject matter of Example 28 may optionally include control circuitry that may be configured to use a neural network to determine when the received electrical signals representing evoked compound action potentials at the first set of electrodes match the received electrical signals representing evoked compound action potentials stored in the memory corresponding to the first set of electrodes.

An example (e.g., "Example 37") of subject matter (e.g., a system) may include recording circuitry configured to receive electrical signals from a first set of electrodes implanted within a patient, the first set of electrodes being configured to receive electrical signals representing evoked compound action potentials generated by the patient in response to stimulation of an external location on the patient's body and to record the received electrical signals in a memory. The system may also include stimulation circuitry configured to apply electrical signals using a second set of electrodes implanted within the patient to provide neuromodulation to the patient. The system may also include control circuitry configured to receive electrical signals representing evoked compound action potentials received at the first set of electrodes and generated by the patient in response to the electrical signals applied by the stimulation circuitry using the second set of electrodes, and to adjust one or more electrical parameters of the electrical signals applied by the stimulation circuitry using the second set of electrodes to increase a correlation between the electrical signals received by the control circuitry and the electrical signals recorded by the recording circuitry.

In Example 37, the subject matter of Example 36 may optionally be configured such that the external location on the patient's body is a dermatomal target and wherein the control circuitry is configured to adjust the one or more electrical parameters of the electrical signals applied to the second set of electrodes to provide stimulation of the dermatomal target.

In Example 38, the subject matter according to any of Examples 36-37 may optionally be configured such that the second set of electrodes includes electrodes on a paddle lead configured to provide spinal cord stimulation.

In Example 39, the subject matter according to any of Examples 36-38 may optionally be configured such that the adjusted one or more electrical parameters include at least one of an amplitude, pulse width, or frequency.

In Example 40, the subject matter according to any of Examples 36-39 may optionally be configured such that the first set of electrodes is located proximal to a dorsal root ganglia of the patient.

In Example 41, the subject matter according to any of Examples 36-40 may optionally be configured such that the first set of electrodes is located in a neural foramen or epidural space of the patient.

In Example 42, the subject matter according to any of Examples 36-41 may optionally be configured such that the control circuitry is configured to instruct the stimulation circuitry to adjust a charge delivered to the second set of electrodes to maintain measured electrical signals representing evoked compound action potentials at the first set of electrodes.

In Example 43, the subject matter according to any of Examples 36-42 may optionally be configured such that the control circuitry is configured to use a matched filter to determine whether the adjusted one or more electrical parameters increases the correlation between the electrical signals received by the control circuitry and the electrical signals recorded by the recording circuitry.

In Example 44, the subject matter according to any of Examples 36-43 may optionally be configured such that the system further comprises neural network circuitry configured to determine whether the adjusted one or more electrical parameters increases the correlation between the electrical signals received by the control circuitry and the electrical signals recorded by the recording circuitry.

In Example 45, the subject matter according to any of Examples 36-44 may optionally be configured such that the control circuitry is configured to form a feature parameter space including one or more features extracted from the recorded evoked compound action potentials.

In Example 46, the subject matter according to any of Examples 36-45 may optionally be configured such that the control circuitry is configured to use a feature set comparison to determine whether the adjusted one or more electrical parameters increases the correlation between the electrical signals received by the control circuitry and the electrical signals recorded by the recording circuitry.

In Example 47, the subject matter according to any of Examples 36-46 may optionally be configured such that the one or more features include one or more of an amplitude, delay, width, or metric associated with an evoked compound action potential.

In Example 48, the subject matter according to any of Examples 36-47 may optionally be configured such that the stimulation circuitry is configured to apply electrical signals using the first set of electrodes implanted within the patient, the applied electrical signals corresponding to evoked compound action potentials recorded by the first set of electrodes.

In Example 49, the subject matter according to any of Examples 36-48 may optionally be configured such that the electrical signals applied using the first set of electrodes stimulate a first neural element of a pain neural network and the electrical signals applied using the second set of electrodes stimulate a second neural element of the pain neural network.

In Example 50, the subject matter according to any of Examples 36-49 may optionally be configured such that the first neural element and the second neural element can include at least one of A beta fibers, inhibitory interneurons, or pain transmission fibers.

An example (e.g., "Example 51") of subject matter (e.g., a method) may include stimulating an external location on a patient's body to generate a first evoked compound action potential. The method may also include receiving electrical signals from a first location, the received electrical signals representing the first evoked compound action potential generated by the patient in response to stimulation of the external location. The method may also include storing the received electrical signals corresponding to the first evoked compound action potential in a memory. The method may also include internally stimulating a location within the patient's body to generate a second evoked compound action potential. The method may also include receiving electrical signals from the first location, the received electrical signals representing the second evoked compound action potential generated by the patient in response to the internal stimulation. The method may also include determining a difference between the received electrical signals representing the second evoked compound action potential to the stored electrical signals corresponding to the first evoked compound action potential. The method may also include adjusting at least one electrical parameter of the internal stimulation to reduce the determined difference between the received electrical signals representing the second evoked compound action potential and the stored electrical signals corresponding to the first evoked compound action potential.

In Example 52, the subject matter of Example 51 may optionally be configured such that stimulating the external location on a patient's body to generate a first evoked compound action potential includes stimulating an external dermatomal target and/or nearby dermatomes.

In Example 53, the subject matter according to any of Examples 51-52 may optionally include adjusting at least one electrical parameter of the internal stimulation to provide neuromodulation to the dermatomal target and/or nearby dermatomes.

In Example 54, the subject matter according to any of Examples 51-53 may optionally be configured such that internally stimulating a location within the patient's body includes using electrodes on a lead to provide spinal cord stimulation.

In Example 55, the subject matter according to any of Examples 51-54 may optionally be configured such that adjusting at least one electrical parameter of the internal stimulation includes adjusting at least one of an amplitude, pulse width, or frequency.

In Example 56, the subject matter according to any of Examples 51-55 may optionally be configured such that receiving electrical signals representing the first evoked compound action potential generated by the patient in response to stimulation of the external location includes receiving electrical signals corresponding to an evoked compound action potential sensed proximal to the dorsal root ganglia.

In Example 57, the subject matter according to any of Examples 51-56 may optionally be configured such that receiving electrical signals representing the first evoked compound action potential generated by the patient in response to stimulation of the external location includes receiving electrical signals corresponding to an evoked compound action potential sensed proximal to the neural foramen.

In Example 58, the subject matter according to any of Examples 51-57 may optionally include using a matched filter to determine a difference between the received electrical signals representing the second evoked compound action potential and the stored electrical signals corresponding to the first evoked compound action potential.

An example (e.g., "Example 59") of subject matter (e.g., a non-transitory machine-readable medium) may include in instructions, which when executed by a machine, cause the machine to stimulate an external location on a patient's body to generate a first evoked compound action potential. The non-transitory machine-readable medium can also include instructions, which when executed by a machine, cause the machine to receive electrical signals from a first location, the received electrical signals representing the first evoked compound action potential generated by the patient in response to stimulation of the external location. The non-transitory machine-readable medium can also include instructions, which when executed by a machine, cause the machine to store the received electrical signals corresponding to the first evoked compound action potential in a memory. The non-transitory machine-readable medium can also include instructions, which when executed by a machine, cause the machine to internally stimulate a location within the patient's body to generate a second evoked compound action potential. The non-transitory machine-readable medium can also include instructions, which when executed by a machine, cause the machine to receive electrical signals from the first location, the received electrical signals representing the second evoked compound action potential generated by the patient in response to the internal stimulation. The non-transitory machine-readable medium can also include instructions, which when executed by a machine, cause the machine to determine a difference between the received electrical signals representing the second evoked compound action potential to the stored electrical signals corresponding to the first evoked compound action potential. The non-transitory machine-readable medium can also include instructions, which when executed by a machine, cause the machine to adjust at least one electrical parameter of the internal stimulation to reduce the determined difference between the received electrical signals representing the second evoked compound action potential and the stored electrical signals corresponding to the first evoked compound action potential.

In Example 60, the subject matter according to Example 59 may optionally include instructions, which when executed by a machine, cause the machine to adjust at least one electrical parameter of the internal stimulation to provide neuromodulation to a dermatomal target stimulated by the stimulation of the external location.

In Example 61, the subject matter according to any of Examples 59-60 may optionally be configured such that adjusting at least one electrical parameter of the internal stimulation includes adjusting at least one of an amplitude, pulse width, or frequency.

In Example 62, the subject matter according to any of Examples 59-61 may optionally include instructions, which when executed by the machine, cause the machine to use a matched filter to determine a difference between the received electrical signals representing the second evoked compound action potential and the stored electrical signals corresponding to the first evoked compound action potential.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Clinically, a neuromodulation system may provide pain relief to a patient. For example, an implanted spinal cord stimulation system may be activated to provide pain relief to various portions of the patient's body. An implanted lead, such as may be used for spinal cord stimulation may include a number of electrodes corresponding to one or more dermatomes on the patient's body. A clinician may determine, such as by trial and error, one or more electrical parameters of at least one electrical waveform to be applied to the electrodes, such as to provide pain relief to a dermatome of the patient. Such a trial and error method may be time consuming and may lead to delayed treatment of the patient.

The inventors have recognized, among other things, that it may be possible to use a closed loop feedback system to determine one or more electrical parameters of at least one electrical waveform to be applied to the electrodes, such as to provide pain relief to the patient.

Current neuromodulation systems may be programmed to deliver waveforms having parameters such as a frequency, amplitude, and pulse width. In a sub-threshold spinal cord stimulation (SCS) system, pain relief may develop after a latent period ranging from hours to days. To determine a set of parameters that provide pain relief, a clinician may set the waveform parameters to experimentally predetermined values. After waiting for a time greater than or equal to the latent period, the patient may provide feedback to the clinician to determine if the delivered waveform is providing pain relief. The clinician may then repeatedly adjust the waveform parameters while waiting for a time greater than or equal to the latent period between each adjustment. Various examples disclosed herein provide a method for optimizing the waveform parameters in a sub-threshold SCS stimulation system.

Figure 1:
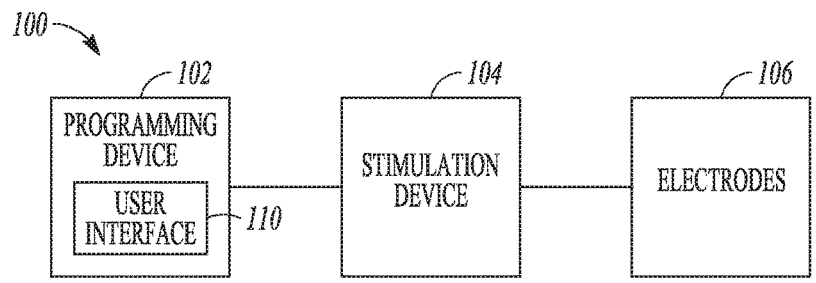
FIG. 1 illustrates an example of a neuromodulation system.

FIG. 1 illustrates an example of a neuromodulation system 100. The neuromodulation system 100 may include electrodes 106, a stimulation device 104, and a programming device 102. The electrodes 106 may be configured to be placed on or near one or more neural targets in a patient. The stimulation device 104 may be configured to be electrically connected to the electrodes 106 and deliver neuromodulation energy, such as in the form of an electrical waveform, to the one or more neural targets though the electrodes 106. The delivery of the neuromodulation may be controlled using a plurality of stimulation parameters, such as stimulation parameters specifying a waveform shape or waveform morphology such as, but not limited to, a pattern of electrical pulses and a selection of electrodes through which each of the electrical pulses may be delivered. At least some parameters of the plurality of stimulation parameters may be programmable by a user, such as a physician or other caregiver who treats the patient using the neuromodulation system 100. Programming device 102 may provide the user with accessibility to the user-programmable parameters. The programming device 102 may be configured to be communicatively coupled to stimulation device 104 via a wired or wireless link. The programming device 102 may receive a signal from the patient and based on the received signal, the programming device 102 may automatically adjust the stimulation parameters, such as to provide improved pain relief to the patient. The received signal may include information about a sensitivity of the patient to delivered neuromodulation energy. In an example where the electrodes may be implanted in the patient, the received signal may include information about the position of the electrodes 106 within the patient.

In an example, the programming device 102 may include a user interface that allows the user to set and/or adjust values of the user-programmable parameters by creating and/or editing graphical representations of various waveforms. Such waveforms may include different waveform shapes. The waveform shapes may include regular shapes (e.g. square, sinusoidal, triangular, saw tooth, and the like) or irregular shapes. Such waveforms may include, for example, a pattern of neuromodulation pulses to be delivered to the patient as well as waveform building blocks that may be used in the pattern of neuromodulation pulses. Examples of such waveform building blocks may include pulses, bursts each including a group of the pulses, trains each including a group of the bursts, and sequences each including a group of the pulses, bursts, and trains, as further discussed below. In various embodiments, programming device 102 allows the user to edit existing waveform building blocks, create new waveform building blocks, import waveform building blocks created by other users, and/or export waveform building blocks to be used by other users. The user may also be allowed to define an electrode selection specific to each waveform building block. In the illustrated embodiment, the user interface may include a user interface 110. In various embodiments, the user interface 110 may include a GUI or any other type of user interface accommodating various functions including waveform composition as discussed in this document. In an example, the programming device 102 may receive a waveform file. The waveform file may include a waveform shape or a sequence of waveform building blocks. In an example, the programming device may receive a target location for the neuromodulation energy. The neuromodulation system 100 may deliver an electrical waveform to the received target location, and the electrical waveform may have a shape according to a received waveform file.

Figure 2:
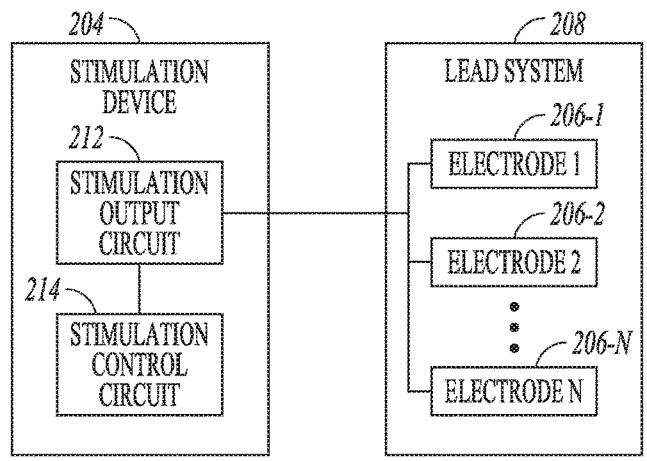
FIG. 2 illustrates an example of a stimulation device and a lead system.

FIG. 2 illustrates an example of a stimulation device 204 and a lead system 208, such as may be implemented in the neuromodulation system 100. The stimulation device 204 may represent an example of the stimulation device 104 and may include a stimulation output circuit 212 and a stimulation control circuit 214. The stimulation output circuit 212 may produce and deliver a neuromodulation waveform. Such waveforms may include different waveform shapes. The waveform shapes may include regular shapes (e.g. square, sinusoidal, triangular, saw tooth, and the like) or irregular shapes. The stimulation control circuit 214 may control the delivery of the neuromodulation waveform using the plurality of stimulation parameters, which specifies a pattern of the neuromodulation waveform. The lead system 208 may include one or more leads each configured to be electrically connected to stimulation device 204 and a plurality of electrodes 206 distributed in the one or more leads. The plurality of electrodes 206 may include electrode 206-1, electrode 206-2, . . . electrode 206-N, each a single electrically conductive contact providing for an electrical interface between the stimulation output circuit 212 and the tissue of the patient, where N≥2. The neuromodulation waveform may be delivered from stimulation output circuit 212 through a set of electrodes selected from electrodes 206.

In an example, the number of leads and the number of electrodes on each lead depend on, for example, the distribution of target(s) of the neuromodulation and the need for controlling the distribution of electric field at each target. In an example, the lead system 208 includes 2 leads each having 8 electrodes.

Figure 3:
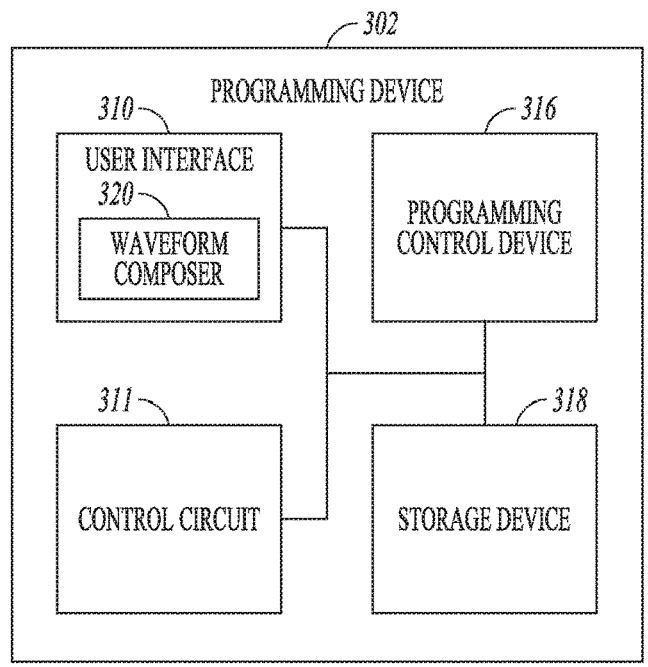
FIG. 3 illustrates an example of a programming device.

FIG. 3 illustrates an example of a programming device 302, such as may be implemented in the neuromodulation system 100. The programming device 302 may represent an embodiment of the programming device 102 and may include a storage device 318, a programming control circuit 316, a control circuit 311 and a user interface 310. The storage device 318 may store a plurality of waveform building blocks. The programming control circuit 316 may generate a plurality of stimulation parameters that control the delivery of the neuromodulation waveform according to the pattern of the neuromodulation waveform. The control circuit 311 may receive a signal and may adjust the values of the plurality of stimulation parameters based on the received signal. The received signal may include information about a patient sensitivity to delivered neuromodulation (e.g., information about an intensity or location of the delivered neuromodulation). The control circuit 311 may determine at least one stimulation parameter based on the information about the patient sensitivity. The received signal may include information about a position of an electrode relative to the patient. The electrode may be an implanted electrode within the patient or may be external to the patient. The control circuit 311 may determine at least one stimulation parameter based on the position of the electrode relative to the patient. The user interface 310 may represent an embodiment of the user interface 110 and allow the user to compose the waveform building blocks and compose the pattern of the neuromodulation waveform using one or more waveform building blocks selected from the plurality of waveform building blocks.

In an example, the user interface 310 may include a waveform composer 320 that allows the user to manage the waveform building blocks, including creating and importing waveform building blocks to be added to the waveform building blocks stored in storage device 318, exporting waveform building blocks selected from the waveform building blocks stored in storage device 318, and editing each of the waveform building blocks. In an example, the user interface 310 may include a GUI that allows for graphical editing of each of the waveform building blocks. In an example, the waveform composer 320 may allow the user to compose the pattern of the neuromodulation waveform to be delivered to the patent by the stimulation device 104 using waveform building blocks such as, but not limited to pulses, bursts each including a group of the pulses, trains each including a group of the bursts, and/or sequences each including a group of the pulses, bursts, and trains. In an example, the waveform composer 320 may allow the user to create each waveform building block using one or more waveform building blocks stored in the storage device 318 as templates. In an example, the waveform composer 320 may allow each newly created waveform building block to be saved as an additional waveform building block stored in the storage device 318.

In an example, the user interface 310 may include, but is not limited to, a touchscreen. In an example, the user interface 310 may include any type of presentation device, such as interactive or non-interactive screens, and any type of user input devices that allow the user to edit the waveforms or building blocks and schedule the programs, such as touchscreen, keyboard, keypad, touchpad, trackball, joystick, and mouse. In an example, the circuits of neuromodulation system 100, including its various embodiments discussed in this document, may be implemented using a combination of hardware and software. For example, the circuit of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit may include, but is not limited to, a microprocessor or a portion thereof, a microcontroller or portions thereof, and a programmable logic circuit or a portion thereof.

Figure 4:
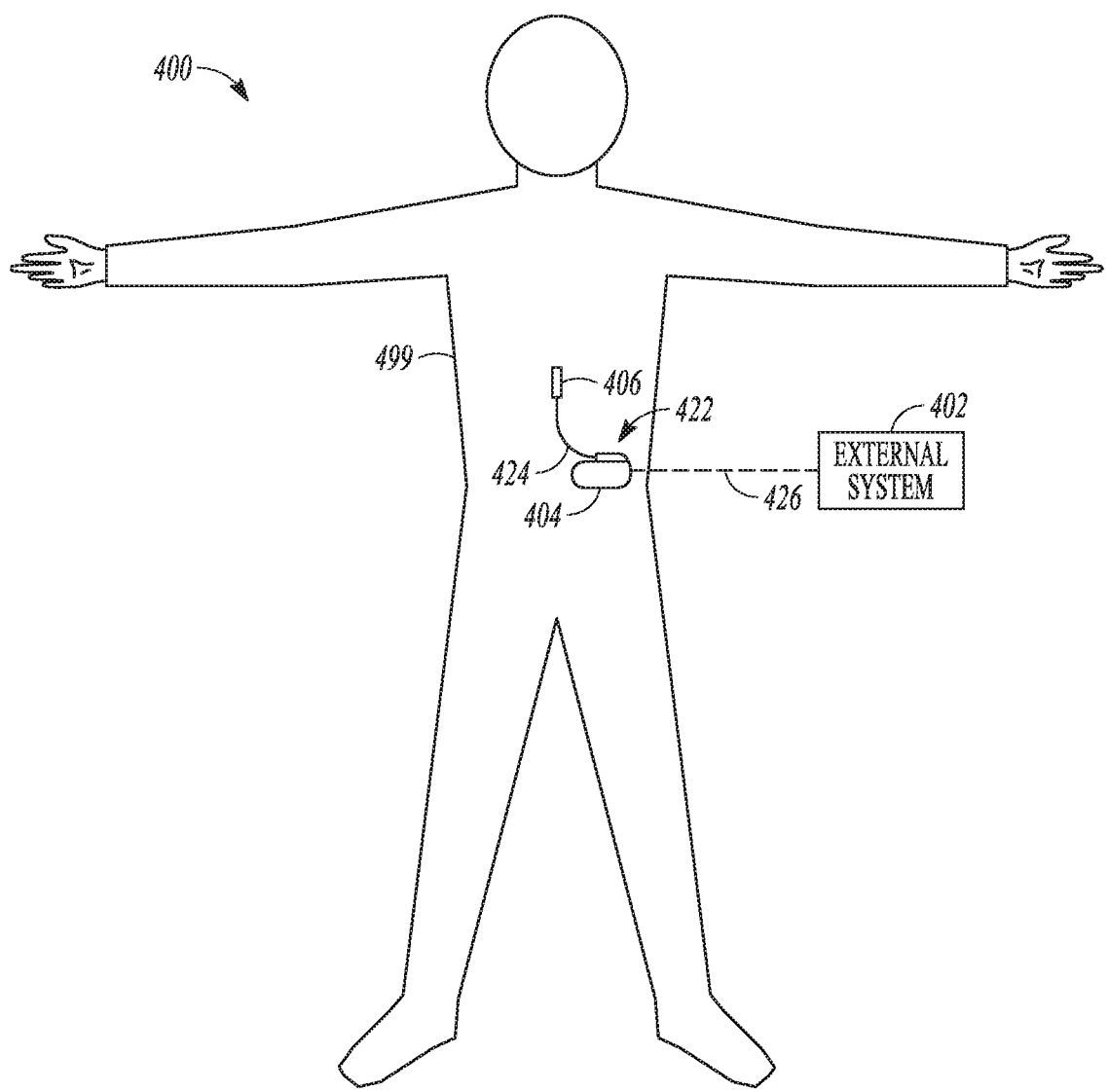
FIG. 4 illustrates an example of an implantable neuromodulation system.

FIG. 4 illustrates, by way of example and not limitation, an implantable neuromodulation system 400 and portions of an environment in which system 400 may be used. The system 400 may include an implantable system 422, an external system 402, and a telemetry link 426 providing for wireless communication between implantable system 422 and external system 402. The implantable system 422 is illustrated in FIG. 4 as being implanted in the patient's body 499.

The implantable system 422 may include an implantable stimulator (also referred to as an implantable pulse generator, or IPG) 404, a lead system 424, and electrodes 406, which may represent an embodiment of stimulation device 204, lead system 208, and electrodes 206, respectively. The external system 402 may represent an embodiment of programming device 302. In an example, the external system 402 includes one or more external (non-implantable) devices each allowing the user and/or the patient to communicate with implantable system 422. In an example, the external system 402 may include a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters.

The sizes and shapes of the elements of the implantable system 422 and their location in the body 499 are illustrated by way of example and not by way of restriction. In various examples, the present subject matter may be applied in programming any type of stimulation device that uses electrical waveforms or electrical pulses as stimuli, regardless of stimulation targets in the patient's body and whether the stimulation device is implantable.

Figure 5:
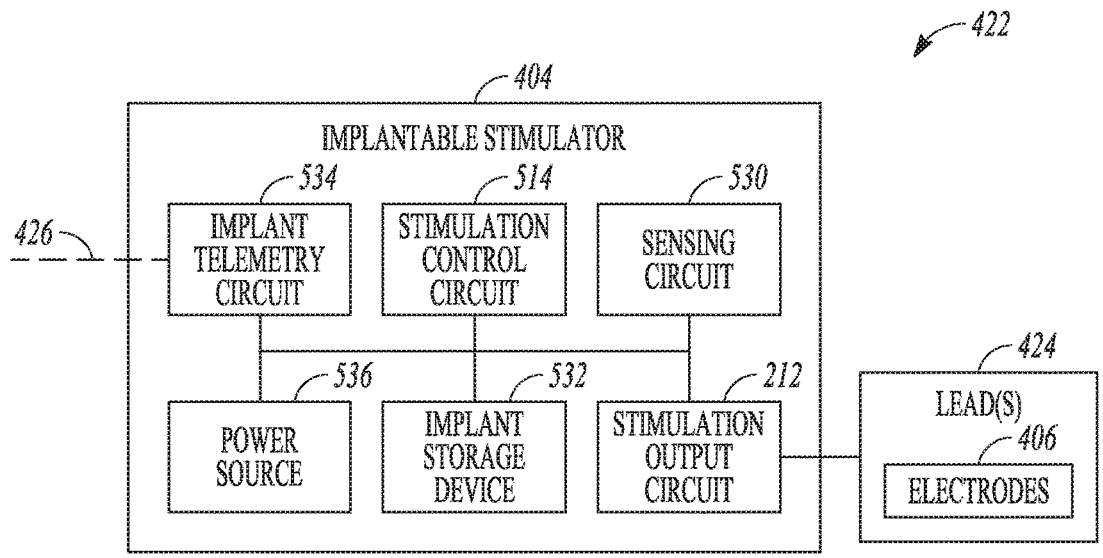
FIG. 5 illustrates an example of an implantable stimulator and one or more leads of an implantable neuromodulation system.

FIG. 5 illustrates, by way of example and not limitation, an example of the implantable stimulator 404 and one or more leads 424 of an implantable neuromodulation system, such as the implantable system 422. Implantable stimulator 404 may include a sensing circuit 530 that is optional and required only when the stimulator has a sensing capability, a stimulation output circuit 212, a stimulation control circuit 514, an implantable storage device 532, an implantable telemetry circuit 534, and a power source 536. The sensing circuit 530, when included and needed, may sense one or more physiological signals, such as for the purposes of patient monitoring and/or feedback control of the neuromodulation. Examples of the one or more physiological signals may include neural and other signals each indicative of a condition of the patient that is treated by the neuromodulation and/or a response of the patient to the delivery of the neuromodulation. The sensing circuit 530 may sense an impedance of at least one electrode delivering neuromodulation to the patient. The sensing circuit 530 may provide the sensed impedance to the control circuit 611, such as via the telemetry link 426. The stimulation output circuit 212 may be electrically connected to the electrodes 406 through the lead 424, and may deliver the neuromodulation through a set of electrodes selected from electrodes 406. The stimulation control circuit 514 may represent an embodiment of the stimulation control circuit 214 and may control the delivery of the neuromodulation using the plurality of stimulation parameters specifying a waveform shape or a pattern of neuromodulation pulses. In an example, the stimulation control circuit 514 may control the delivery of the neuromodulation using the one or more sensed physiological signals. The implant telemetry circuit 534 may provide the implantable stimulator 404 with wireless communication with another device such as a device of external system 402, including receiving values of the plurality of stimulation parameters from external system 402. The implant storage device 532 may store values of the plurality of stimulation parameters. The power source 536 may provide the implantable stimulator 404 with energy for its operation. In an example, the power source 536 includes a battery. In an example, the power source 536 includes a rechargeable battery and a battery charging circuit for charging the rechargeable battery. The implant telemetry circuit 534 may also function as a power receiver that receives power transmitted from external system 402 through an inductive couple.

In various examples, the sensing circuit 530 (if included), the stimulation output circuit 212, the stimulation control circuit 514, the implant telemetry circuit 534, the implant storage device 532, and the power source 536 are encapsulated in a hermetically sealed implantable housing. In various examples, the lead(s) 424 may be implanted such that the electrodes 406 are placed on and/or around one or more targets to which the neuromodulation is to be delivered, while implantable stimulator 404 is subcutaneously implanted and connected to lead(s) 424 at the time of implantation.

Figure 6:
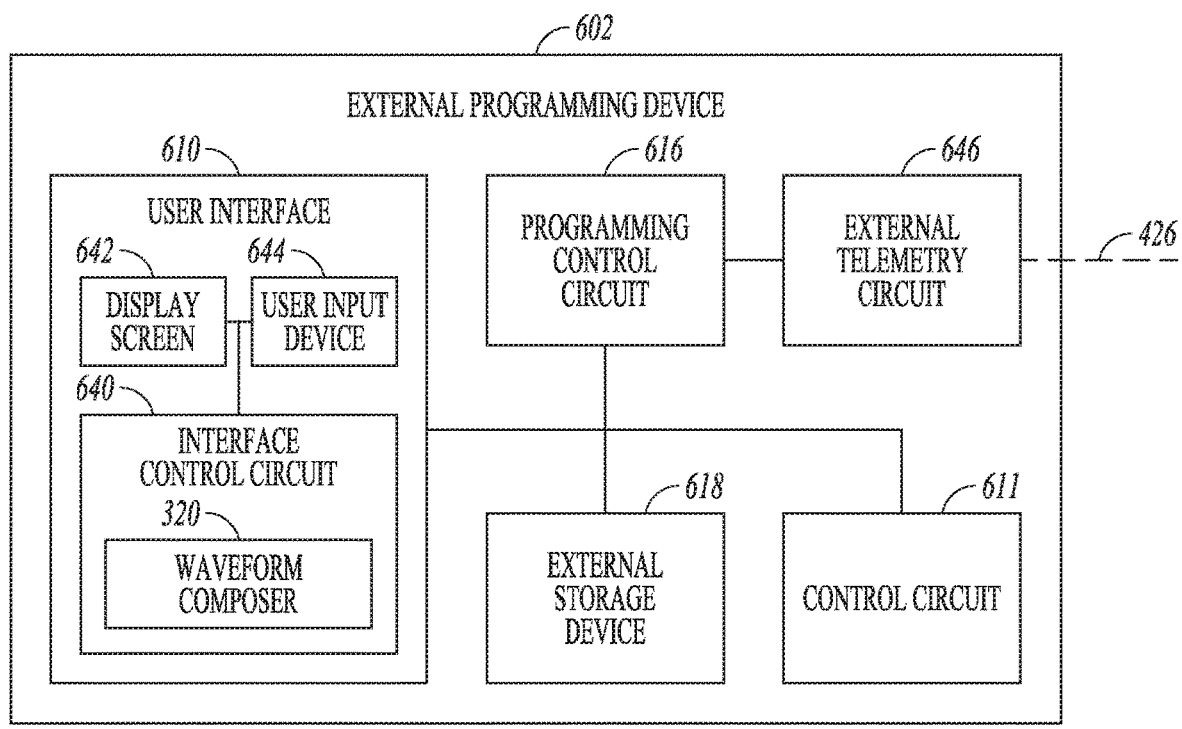
FIG. 6 illustrates an example of an external programming device of an implantable neuromodulation system.

FIG. 6 illustrates an example of an external programming device 602 of an implantable neuromodulation system, such as the external system 402. The external programming device 602 may represent an embodiment of the programming device 302, and may include an external telemetry circuit 646, an external storage device 618, a programming control circuit 616, a control circuit 611, and a user interface 610.

The external telemetry circuit 646 may provide the external programming device 602 with wireless communication with another device such as the implantable stimulator 404 via telemetry link 426, including transmitting the plurality of stimulation parameters to the implantable stimulator 404. In one embodiment, the external telemetry circuit 646 also transmits power to the implantable stimulator 404 through the inductive couple.

The external storage device 618 may store a plurality of waveform building blocks each selectable for use as a portion of the pattern of the neuromodulation. In various embodiments, each waveform building block of the plurality of waveform building blocks includes one or more waveform shape of the neuromodulation, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. The external storage device 618 may also store a plurality of stimulation fields. Each waveform building block of the plurality of waveform building blocks may associated with one or more fields of the plurality of stimulation fields. Each field of the plurality of stimulation fields may be defined by one or more electrodes of the plurality of electrodes through which the neuromodulation may be delivered and a current distribution of the pulse over the one or more electrodes.

The programming control circuit 616 represents an embodiment of the programming control circuit 316 and may generate the plurality of stimulation parameters, which may be transmitted to the implantable stimulator 404, according to the pattern of the neuromodulation. The pattern may be defined using one or more waveform building blocks selected from the plurality of waveform building blocks stored in the external storage device 618. In various embodiment, the programming control circuit 616 may check values of the plurality of stimulation parameters against safety rules to limit these values within constraints of the safety rules. In an example, the safety rules are heuristic rules.

The user interface 610 may represent an embodiment of the user interface 310 and may allow the user to define the pattern of neuromodulation pulses and perform various other monitoring and programming tasks. In an example, the user interface 610 includes a GUI. The user interface 610 includes a display screen 642, a user input device 644, and an interface control circuit 640. The display screen 642 may include any type of interactive or non-interactive screens, and the user input device 644 may include any type of user input devices that supports the various functions discussed in this document, such as touchscreen, keyboard, keypad, touchpad, trackball, joystick, and mouse. In an example, the user interface 610 may include a GUI that has an interactive screen for displaying a graphical representation of a waveform building block and may allow the user to adjust the waveform building block by graphically editing the waveform building block. The user interface 610 may also allow the user to perform any other functions discussed in this document where graphical editing is suitable as may be appreciated by those skilled in the art.

The interface control circuit 640 may control the operation of the user interface 610 including responding to various inputs received by the user input device 644 and defining the one or more stimulation waveforms. The interface control circuit 640 may include the waveform composer 320.

The external programming device 602 may have operation modes including a composition mode and a real-time programming mode. In the composition mode (also known as the pulse pattern composition mode), the user interface 610 may be activated, while the programming control circuit 616 may be deactivated. In an example, the programming control circuit 616 does not dynamically update values of the plurality of stimulation parameters in response to any change in the one or more stimulation waveforms. In the real-time programming mode, both the user interface 610 and the programming control circuit 616 may be activated. The programming control circuit 616 may dynamically update values of the plurality of stimulation parameters in response to changes in the set of one or more stimulation waveforms, and transmit the plurality of stimulation parameters with the updated values to the implantable stimulator 404. The control circuit 611 may receive a signal and may adjust the values of the plurality of stimulation parameters based on the received signal. The received signal may include information about a patient sensitivity to the stimulation waveform. The control circuit 611 may determine at least one stimulation parameter based on the information about the patient sensitivity to the stimulation waveform. The received signal may include a sensed impedance received from the sensing circuit 530. The control circuit may determine a relative electrode position based on the received sensed impedance received from the sensing circuit 530. The received signal may include an imaging signal received from an imaging device. The control circuit may determine a relative electrode position based on the received signal from the imaging device. The electrode may be an implanted electrode within the patient or may be external to the patient. The control circuit 611 may determine at least one stimulation parameter based on the determined relative position of the electrode.

Figure 7:
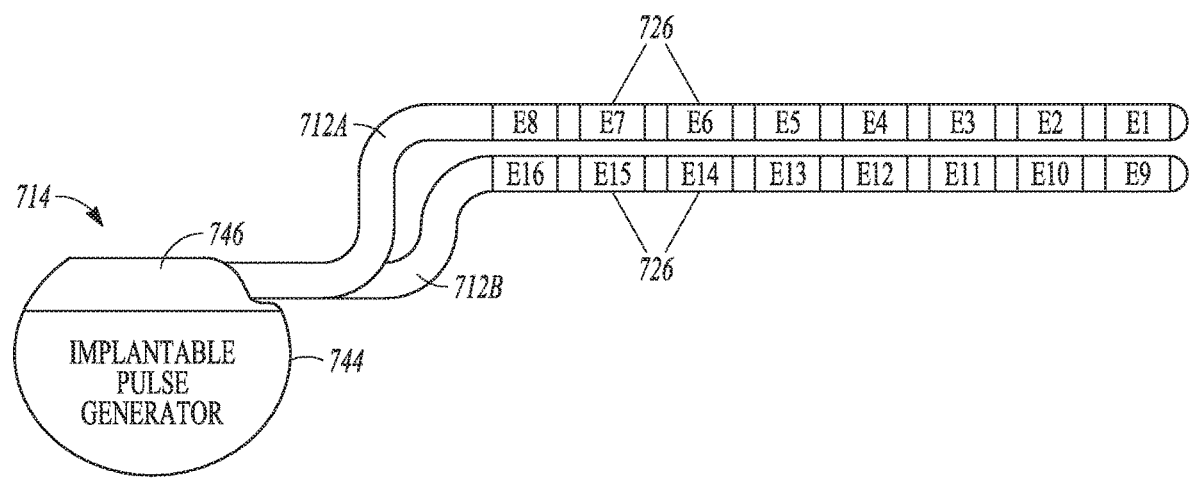
FIG. 7 illustrates an example of an implantable pulse generator (IPG) and percutaneous leads.

FIG. 7 illustrates, by way of example and not limitation, an example of a profile view of an implantable pulse generator (IPG) 744 and percutaneous leads 712. One of the neuromodulation leads 712a may have eight electrodes 726 (labeled E1-E8), and the other neuromodulation lead 712b may have eight electrodes 726 (labeled E9-E16). The actual number and shape of leads and electrodes may, of course, vary according to the intended application. The IPG 14 may comprise an outer case 744 for housing the electronic and other components (described in further detail below), and a connector 746 to which the proximal ends of the neuromodulation leads 712 mates in a manner that electrically couples the electrodes 726 to the electronics within the outer case 744. The outer case 744 may be composed of an electrically conductive, biocompatible material, such as titanium, and forms a hermetically sealed compartment wherein the internal electronics are protected from the body tissue and fluids. In some examples, the outer case 744 may serve as an electrode.

In an example, the IPG 714 includes a battery and pulse generation circuitry that delivers the electrical modulation energy in the form of one or more electrical pulse trains to the electrode array 726 in accordance with a set of modulation parameters programmed into the IPG 714. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters that may define the pulse amplitude (which may be measured in milliamps or volts depending on whether the IPG 714 supplies constant current or constant voltage to the electrode array 726), pulse duration (which may be measured in microseconds), pulse rate (which may be measured in pulses per second), and burst rate (which may be measured as the modulation on duration X and modulation off duration Y).

In an example, electrical modulation may occur between two (or more) activated electrodes, one of which may be the IPG case 744. Modulation energy may be transmitted to the tissue in a monopolar or multipolar (e.g., bipolar, tripolar, etc.) fashion. Monopolar modulation may occur when a selected one of the lead electrodes 726 is activated along with the case of the IPG 714, so that modulation energy is transmitted between the selected electrode 726 and case. Bipolar modulation may occur when two of the lead electrodes 726 are activated as anode and cathode, so that modulation energy is transmitted between the selected electrodes 726. For example, electrode E3 on the first lead 712a may be activated as an anode at the same time that electrode E11 on the second lead 712a is activated as a cathode. Tripolar modulation may occur when three of the lead electrodes 726 are activated, two as anodes and the remaining one as a cathode, or two as cathodes and the remaining one as an anode. For example, electrodes E4 and E5 on the first lead 712a may be activated as anodes at the same time that electrode E12 on the second lead 712b is activated as a cathode. The modulation energy may be delivered between a specified group of electrodes as monophasic electrical energy or multiphasic electrical energy.

Figure 8:
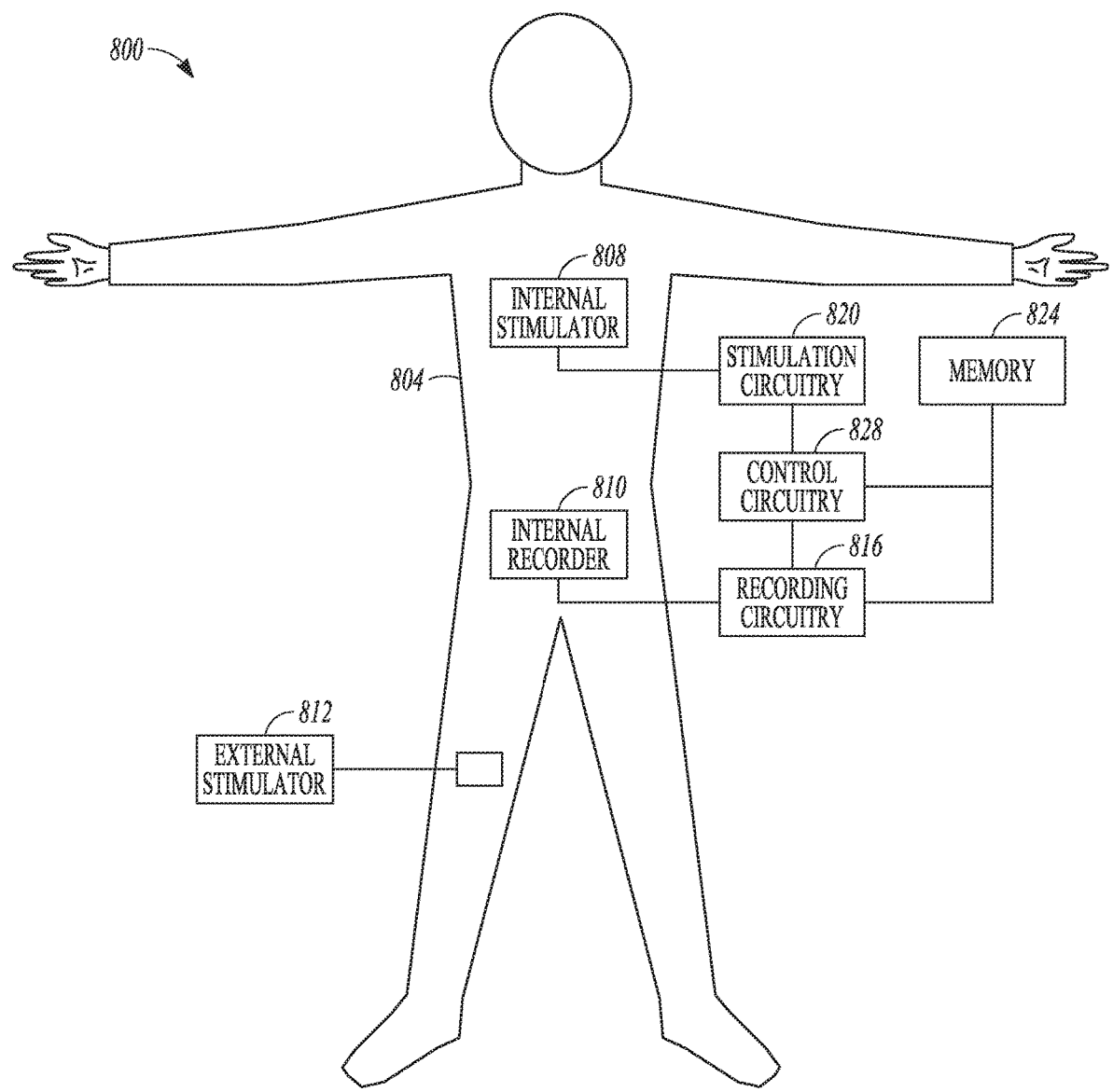
FIG. 8 illustrates an example of a system for providing pain relief to a patient.

FIG. 8 illustrates an example of a system for providing pain relief to a patient. The system may include an internal stimulator 808, an internal recorder 810, an external stimulator 812, recording circuitry 816, stimulation circuitry 820, memory 824, and control circuitry 828. The recording circuitry 816 may be connected to the internal recorder 810, the control circuitry 828, and the memory 824. The stimulation circuitry 820 may be connected to the internal stimulator 808, the control circuitry 828, and the memory 824. The internal recorder 810 may be in a different location than the internal stimulator 808. During operation, the external stimulator 812 may be used to apply external stimulation to a region where a patient 804 may be experiencing pain. The external stimulation may include, among other things, thermal stimulation, electrical stimulation, chemical, optical, or mechanical stimulation. The region where the patient may be experiencing pain may correspond to one or more dermatomes. The external stimulation may cause one or more evoked compound action potentials to be produced by the patient's nervous system. The one or more evoked compound action potentials may be sensed by the internal recorder 810 and provided to the recording circuitry 816 as an electrical waveform. The recording circuitry 816 may include amplifiers, filters, and any other signal conditioning components necessary to improve a signal to noise ratio of the sensed one or more evoked compound action potentials. The recording circuitry 816 may then store the one or more evoked compound action potentials in the memory 824. Next, the stimulation circuitry may provide an electrical signal to the internal stimulator 808. The internal stimulator 808 may include one or more electrodes, such as may receive the electrical signal provided by the stimulation circuitry 820 and provide neuromodulation to the patient. The neuromodulation provided to the patient by the internal stimulator 808 may cause one or more evoked compound action potentials to be produced by the patient's nervous system. The control circuitry 828 may compare the one or more evoked compound action potentials caused by the internal stimulator 808 to the one or more evoked compound action potentials stored in the memory 824. The control circuitry 828 may then adjust one or more electrical parameters of the electrical signal provided by the stimulation circuitry 820, such as to reduce a difference between the evoked compound action potentials caused by the internal stimulator 808 and the evoked compound action potentials caused by the external stimulator 812 that may be stored in the memory 824. In an example where the electrical signal may include a pulsed waveform, the one or more electrical parameters may include at least one of an amplitude, frequency, pulse width, cycling (consecutive periods with stimulation on and off), or duty cycle. The electrical parameters may also include electrode combinations, which may define the electrodes that are activated as anodes (positive), cathodes (negative), and turned off (zero), percentage of modulation energy assigned to each electrode (fractionalized electrode configurations).

Figure 9A:
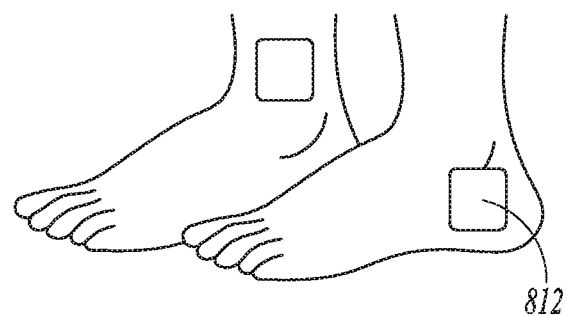
FIG. 9A illustrates an example of an external stimulator.
Figure 9B:
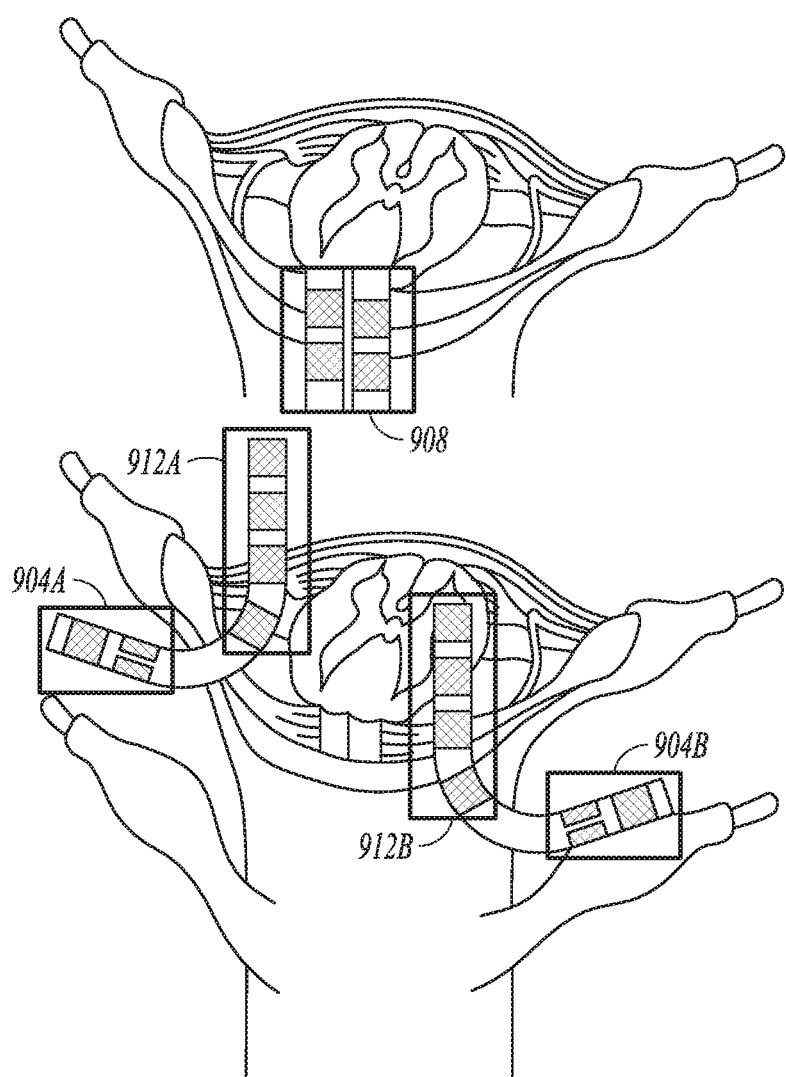
FIG. 9B illustrates an example of an internal stimulator.

FIG. 9A illustrates an example of an external stimulator 812. The external stimulator 812 may be a patch applied to a patient's foot. The patch may provide at least one of electrical, thermal, chemical, optical, ultrasound, or mechanical stimulation. The stimulation provided by the external stimulator may produce evoked compound action potentials within the patient. One or more electrodes, such as directional electrodes 904 may be implanted outside of the neural foramen and proximal to a dorsal root ganglia of the patient as illustrated in FIG. 9B. The directional electrodes 904 may also include one or more ring electrodes. The directional electrodes 904 may sense one or more evoked compound action potentials generated by the patient in response to the stimulation provided by the external stimulator 812. The sensed one or more evoked compound action potentials may be provided to recording circuitry, such as recording circuitry 816. An internal stimulator, such as the internal stimulator 808 may then be activated, such as to provide an electrical signal to one or more electrodes, such as spinal cord stimulation electrodes 908 that may be implanted in an epidural space proximal to a spinal cord of the patient. The stimulation electrodes 908 may provide epidural stimulation to the patient. In an example, the stimulation electrodes may be arranged similar to the electrode array 726. In response to the internal stimulation provided by the internal stimulator 808, evoked compound action potentials may be produced within the patient. The directional electrodes 904 may sense the one or more evoked compound action potentials generated by the patient in response to the stimulation provided by the internal stimulator 808. The directional electrodes 904 may sense the one or more evoked compound action potentials in a radial direction. The sensed one or more evoked compound action potentials may then be provided to control circuitry, such as the control circuitry 828. The control circuitry 828 may then determine a difference between the evoked compound action potential corresponding to the external stimulator 812 and the evoked compound action potential corresponding to the internal stimulator 808. The difference may be determined by measuring a square difference between the two evoked compound action potentials, such as according to the expression $\int(V_1-V_2)^2$, where $V_1$ may represent the evoked compound action potential corresponding to the external stimulation and $V_2$ may represent the evoked compound action potential corresponding to the internal stimulation. If the difference between the two evoked compound action potentials exceeds a specified criterion, then the control circuitry 828 may adjust at least one parameter of the electrical signals provided by the internal stimulator 808 to the stimulation electrodes 908. In an example where the electrical signals may include a pulsed waveform, the at least one electrical parameter may include at least one of an amplitude, frequency, duty cycle, pulse shape, or pulse modulation shape. After adjusting the at least one parameter, the control circuitry 828 may determine a difference between evoked compound action potential corresponding to the external stimulator 812 and the new evoked compound action potential corresponding to the internal stimulator 808. If the difference between the two evoked compound action potentials exceeds the specified criterion, then the control circuitry 828 may further adjust at least one parameter of the electrical signals provided by the internal stimulator 808 to the stimulation electrodes 908. The process may continue until the difference between the two evoked compound action potentials is less than or equal to the specified criterion. Machine learning (e.g., supervised machine learning) may be used to train a neural network model that may be stored in the memory 824 and the control circuitry 828 may retrieve and use the neural network model when making adjustments to the one or more electrical parameters. In an example where a neural network model is used to adjust the one or more electrical parameters, a number of adjustments may be reduced compared to the case where no neural network model is used.

Rostro-caudal electrodes 912a and 912b may also be provided to sense evoked compound action potentials generated in response to external and internal stimulation of the patient. Rostro-caudal electrodes 912a may be rostral and rostro-caudal electrodes 912b may be caudal. Both sets of rostro-caudal electrodes 912a and 912b may be dorsal. The use of rostro-caudal electrodes 912a and 912b may aid in the detection of unwanted spillover stimulation that may occur when the internal stimulation is applied. For example, if one of rostro-caudal electrodes 912a and 912b registers evoked compound action potentials during external stimulation, the same electrode should be registering these during internal stimulation. If additional ones of the rostro-caudal electrodes 912a and 912b are register the activity during the internal stimulation, but not during the external stimulation, the registering of the activity in the additional contacts of the rostro-caudal electrodes 912a and 912b may correspond to neuromodulation of patient dermatomes where pain relief is not desired. The neuromodulation of patient dermatomes where pain relief is not desired may be reduced, such as by adjusting one or more parameters of the electrical signals provided to the spinal cord stimulation electrodes 908.

In certain examples, external stimulation may be applied and ECAPS may be recorded by a first set of electrodes. The recordings corresponding to the first set of electrodes may then be used to determine a stimulation parameter set for the first set of electrodes. For example, if a recorded signal at a first electrode in the first set of electrodes is relatively high compared to a recorded signal at a second electrode in the first set of electrodes, then a subsequent internal stimulation signal applied to the first set of electrodes may include a stimulation signal that may include a relatively larger stimulation signal for the first electrode in the first set of electrodes and a relatively smaller stimulation signal for the second electrode in the second set of electrodes. Such stimulation of the first set of electrodes may increase or decrease (e.g., minimize or maximize) activity of a first portion of a pain neural network (e.g., A beta fibers, inhibitory interneurons, and pain transmission fibers). Additionally, stimulation may be applied to a second set of electrodes, such as may be determined by matching the ECAPS recorded at the first set of electrodes or by increasing a correlation between the recorded ECAPS and ECAPS produced by the first set of electrodes. Such stimulation by the second set of electrodes may target a second portion of the pain neural network different from the first portion of the pain neural network.

Figure 10A:
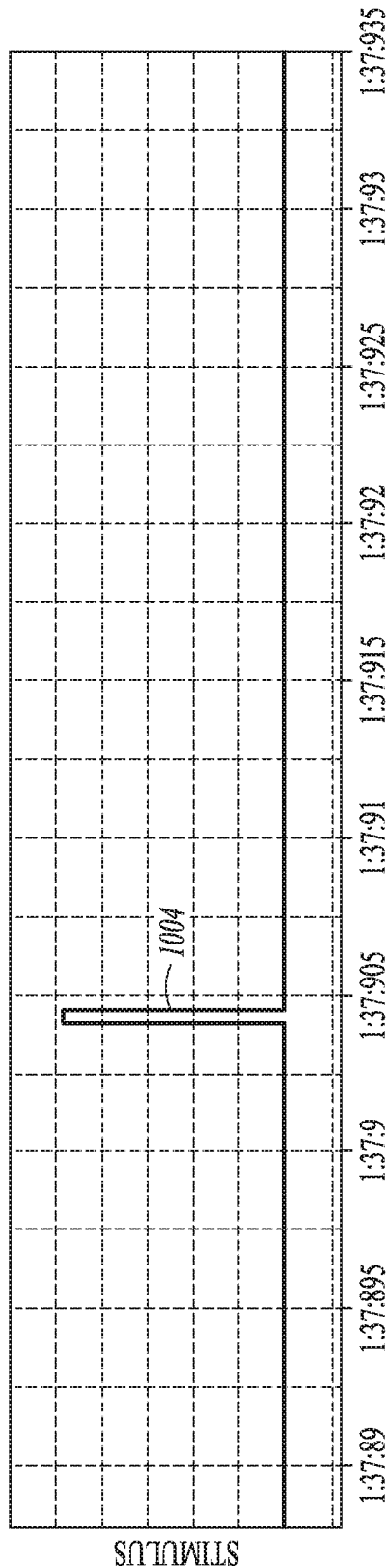
FIG. 10A illustrates an example of a stimulus.
Figure 10B:
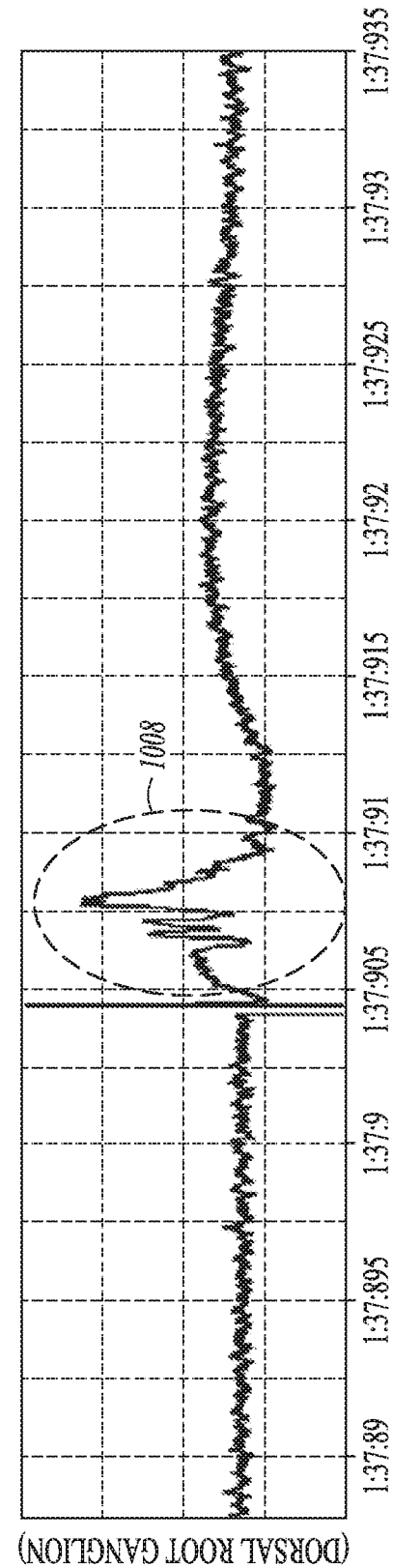
FIG. 10B illustrates an example of an evoked compound action potential.

FIG. 10A illustrates an example of a stimulus 1004 being applied to the patient, such as by the external stimulator 812. The stimulus may include one or more of an electrical, thermal, mechanical, optical, ultrasound, or chemical stimulus. An internal recorder, such as the internal recorder 810 may be located proximal to the dorsal root ganglia of the patient and may sense one or more evoked compound action potentials 1008 as illustrated in FIG. 10B. The one or more evoked compound action potentials 1008 may be produced by the patient in response to the stimulus 1004.

Figure 11A:
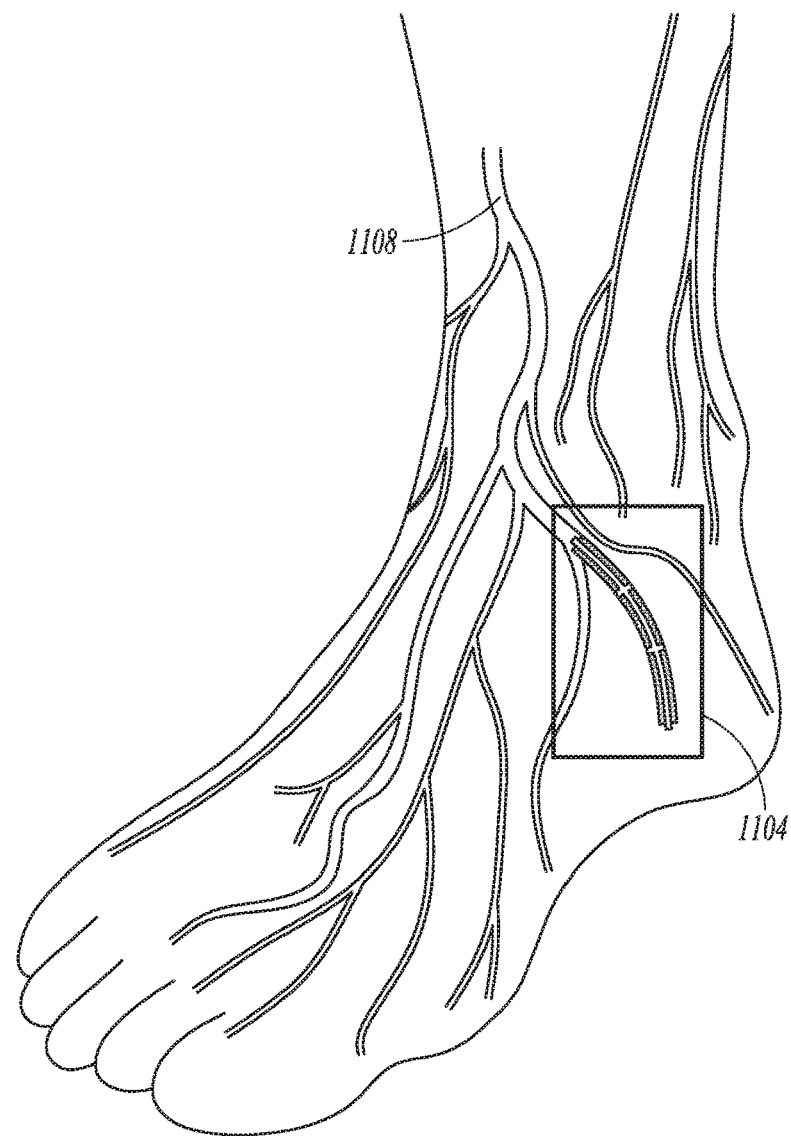
FIG. 11A illustrates and example of an external stimulator.
Figure 11B:
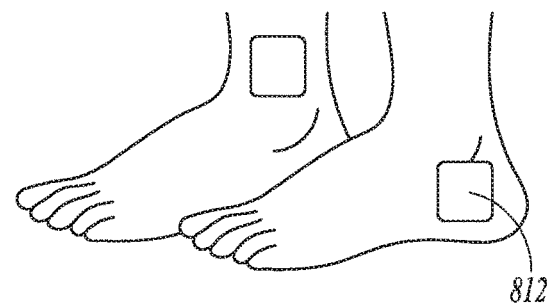
FIG. 11B illustrates an example of an internal stimulator.

FIG. 11A illustrates an example of an external stimulator 812. The external stimulator 812 may be a patch applied to a patient's foot. The patient's foot may include cutaneous nerve trunks 1108. The patch may provide at least one of electrical, thermal, optical, chemical, ultrasound, or mechanical stimulation. The stimulation provided by the external stimulator may produce evoked compound action potentials within the patient. One or more directional electrode, such as directional electrodes 1104 may be implanted proximal to a cutaneous nerve of interest as illustrated in FIG. 11B. A subset of the directional electrodes may be used for stimulation and a subset of the directional electrodes may be used for stimulation. In an example, the same directional electrodes may be used for both stimulation and recording. The cutaneous nerve of interest may include the dorsal lateral cutaneous nerve of a patient's foot. The directional electrodes 1104 may also include one or more ring electrodes. The directional electrodes 904 may sense one or more evoked compound action potentials generated by the patient in response to the stimulation provided by the external stimulator 812. The sensed one or more evoked compound action potentials may be provided to recording circuitry, such as recording circuitry 816. An internal stimulator, such as the internal stimulator 808 may then be activated, such as to provide an electrical signal to one or more electrodes, such as the directional electrodes 1104 that may be implanted proximal to a cutaneous nerve of the patient. The directional electrodes 1104 may provide stimulation to the patient. In response to the internal stimulation provided by the internal stimulator 808, evoked compound action potentials may be produced within the patient. The directional electrodes 1104 may sense the one or more evoked compound action potentials generated by the patient in response to the stimulation provided by the internal stimulator 808. The sensed one or more evoked compound action potentials may then be provided to control circuitry, such as the control circuitry 828. The control circuitry 828 may then determine a difference between the evoked compound action potential corresponding to the external stimulator 812 and the evoked compound action potential corresponding to the internal stimulator 808. The difference may be determined by measuring a square difference between the two evoked compound action potentials, such as according to the expression $\int(V_1-V_2)^2$, where $V_1$ may represent the evoked compound action potential corresponding to the external stimulation and $V_2$ may represent the evoked compound action potential corresponding to the internal stimulation. If the difference between the two evoked compound action potentials exceeds a specified criterion, then the control circuitry 828 may adjust at least one parameter of the electrical signals provided by the internal stimulator 808 to the directional electrodes 1104. In an example where the electrical signals may include a pulsed waveform, the at least one electrical parameter may include at least one of an amplitude, frequency, duty cycle, pulse shape, or pulse modulation shape. After adjusting the at least one parameter, the control circuitry 828 may determine a difference between evoked compound action potential corresponding to the external stimulator 812 and the new evoked compound action potential corresponding to the internal stimulator 808. If the difference between the two evoked compound action potentials exceeds the specified criterion, then the control circuitry 828 may further adjust at least one parameter of the electrical signals provided by the internal stimulator 808 to the directional electrodes 1104. The process may continue until the difference between the two evoked compound action potentials is less than or equal to the specified criterion. Machine learning (e.g., supervised machine learning) may be used to train a neural network model that may be stored in the memory 824 and the control circuitry 828 may retrieve and use the neural network model when making adjustments to the one or more electrical parameters. In an example where a neural network model is used to adjust the one or more electrical parameters, a number of adjustments may be reduced compared to the case where no neural network model is used.

Figure 12:
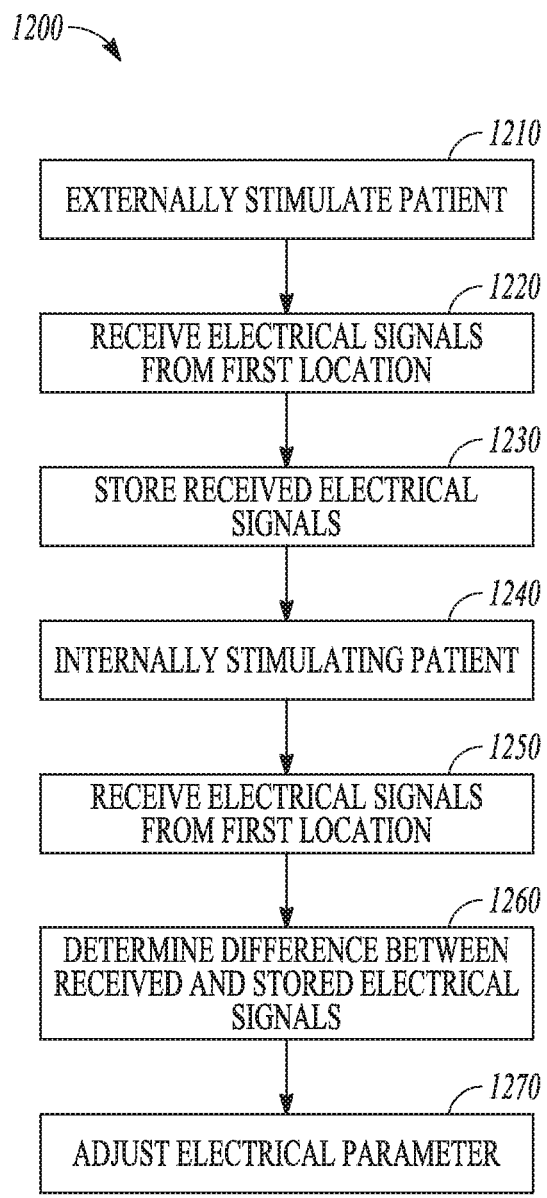
FIG. 12 illustrates a method of providing pain relief to a patient.

FIG. 12 illustrates a method of providing pain relief to a patient. External stimulation may be applied to the patient (step 1210). The external stimulation may be electrical, mechanical, thermal, or chemical. Evoked compound action potentials may be produced within the patient in response to the applied external stimulation. Electrical signals corresponding to the evoked compound action potentials produced in response to the external stimulation may be received at a first location within the patient (step 1220). The electrical signals may be received by one or more electrodes, such as may be implanted epidurally in the patient, or implanted proximal to a cutaneous nerve of interest in the patient. The received electrical signals may be stored in a memory. Internal stimulation may be applied to the patient (step 1240). The internal stimulation may be internal stimulation applied to one or more stimulation electrodes implanted within the patient. Evoked compound action potentials may be produced within the patient in response to the applied internal stimulation. Electrical signals corresponding to the evoked compound action potentials produced in response to the internal stimulation may be received at the first location within the patient (step 1250). A difference may be determined between the received electrical signals corresponding to evoked compound action potentials produced in response to the internal stimulation and the stored electrical signals corresponding to evoked compound action potentials produced in response to the external stimulation (step 1260). The difference may be determined, such as by using a matched filter. One or more features may also be extracted from the ECAP to create a feature parameter space and using machine learning techniques like neural networks, or a simple feature set comparison, then based on the feature map differences the stimulation parameter is changed to reduce the differences. Alternatively, a single feature may be chosen as the landmark to minimize the differences. Note that a feature may be any signal processing metric extracted from the ECAP signal, such as the ECAP amplitude, delay, width, length of the curve as if measuring distance or any measure indicative of distance (e.g., the sum of absolute values of consecutive signal samples over a predefined moving window), area under the curve, ratio of specific amplitudes within the ECAP pattern, or any other signal processing manipulation. At least one electrical parameter may be adjusted to reduce a difference between the received electrical signals corresponding to evoked compound action potentials produced in response to the internal stimulation and the stored electrical signals corresponding to evoked compound action potentials produced in response to the external stimulation (step 1270).

Figure 13:
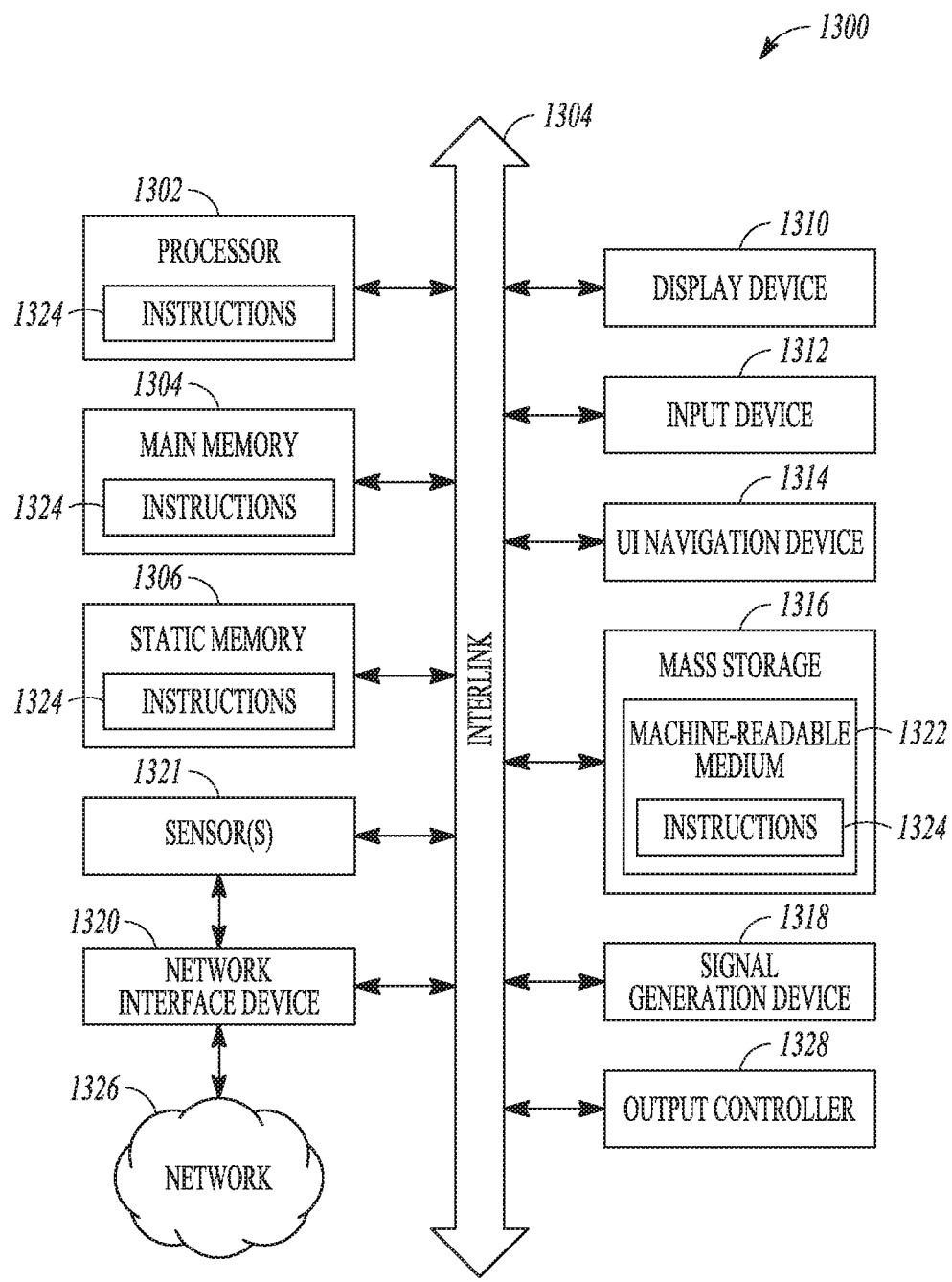
FIG. 13 illustrates generally a block diagram of a machine.

FIG. 13 illustrates generally a block diagram of an example machine 1300 upon which any one or more of the techniques (e.g., methodologies) discussed herein may perform. Portions of this description may apply to the computing framework of various portions of the LCP device, the IMD, or the external programmer.

In alternative embodiments, the machine 1300 may operate as a standalone device or may be connected (e.g., networked) to other machines. In a networked deployment, the machine 1300 may operate in the capacity of a server machine, a client machine, or both in server-client network environments. In an example, the machine 1300 may act as a peer machine in peer-to-peer (P2P) (or other distributed) network environment. The machine 1300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1300 may include a hardware processor 1302 (e.g., a central processing unit (CPU), a graphics processing unit (GPU), a hardware processor core, or any combination thereof), a main memory 1304 and a static memory 1306, some or all of which may communicate with each other via an interlink (e.g., bus) 1308. The machine 1300 may further include a display unit 1310 (e.g., a raster display, vector display, holographic display, etc.), an alphanumeric input device 1312 (e.g., a keyboard), and a user interface (UI) navigation device 1314 (e.g., a mouse). In an example, the display unit 1310, input device 1312 and UI navigation device 1314 may be a touch screen display. The machine 1300 may additionally include a storage device (e.g., drive unit) 1316, a signal generation device 1318 (e.g., a speaker), a network interface device 1320, and one or more sensors 1321, such as a global positioning system (GPS) sensor, compass, accelerometer, or other sensor. The machine 1300 may include an output controller 1328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1316 may include a machine readable medium 1322 on which is stored one or more sets of data structures or instructions 1324 (e.g., software) embodying or utilized by any one or more of the techniques or functions described herein. The instructions 1324 may also reside, completely or at least partially, within the main memory 1304, within static memory 1306, or within the hardware processor 1302 during execution thereof by the machine 1300. In an example, one or any combination of the hardware processor 1302, the main memory 1304, the static memory 1306, or the storage device 1316 may constitute machine readable media.

While the machine readable medium 1322 is illustrated as a single medium, the term "machine readable medium" may include a single medium or multiple media (e.g., a centralized or distributed database, and/or associated caches and servers) configured to store the one or more instructions 1324.

The term "machine readable medium" may include any medium that is capable of storing, encoding, or carrying instructions for execution by the machine 1300 and that cause the machine 1300 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1324 may further be transmitted or received over a communications network 1326 using a transmission medium via the network interface device 1320 utilizing any one of a number of transfer protocols (e.g., frame relay, internet protocol (IP), transmission control protocol (TCP), user datagram protocol (UP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1320 may include one or more physical jacks (e.g., Ethernet, coaxial, or phone jacks) or one or more antennas to connect to the communications network 1326. In an example, the network interface device 1320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1300, and includes digital or analog communications signals or other intangible medium to facilitate communication of such software.

Various embodiments are illustrated in the figures above. One or more features from one or more of these embodiments may be combined to form other embodiments.

Method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A method comprising:
   stimulating an external location on a patient's body to generate a first evoked compound action potential;
   receiving electrical signals from a first location within the patient's body, the received electrical signals representing the first evoked compound action potential generated by the patient in response to stimulation of the external location;
   storing the received electrical signals corresponding to the first evoked compound action potential in a memory;
   internally stimulating a location within the patient's body to generate a second evoked compound action potential;
   receiving electrical signals from the first location, the received electrical signals representing the second evoked compound action potential generated by the patient in response to the internal stimulation;
   determining a difference between the received electrical signals representing the second evoked compound action potential to the stored electrical signals corresponding to the first evoked compound action potential; and
   adjusting at least one electrical parameter of the internal stimulation to reduce the determined difference between the received electrical signals representing the second evoked compound action potential and the stored electrical signals corresponding to the first evoked compound action potential.

2. The method of claim 1 wherein stimulating the external location on a patient's body to generate a first evoked compound action potential includes stimulating an external dermatomal target and/or nearby dermatomes.

3. The method of claim 2 further comprising adjusting at least one electrical parameter of the internal stimulation to provide neuromodulation to the dermatomal target and/or nearby dermatomes.

4. The method of claim 1 wherein internally stimulating a location within the patient's body includes using electrodes on a lead to provide spinal cord stimulation.

5. The method of claim 1 wherein adjusting at least one electrical parameter of the internal stimulation includes adjusting at least one of an amplitude, pulse width, or frequency.

6. The method of claim 1 wherein receiving electrical signals representing the first evoked compound action potential generated by the patient in response to stimulation of the external location includes receiving electrical signals corresponding to an evoked compound action potential sensed proximal to the dorsal root ganglia.

7. The method of claim 1 wherein receiving electrical signals representing the first evoked compound action potential generated by the patient in response to stimulation of the external location includes receiving electrical signals corresponding to an evoked compound action potential sensed proximal to the neural foramen.

8. The method of claim 1 further comprising using a matched filter to determine a difference between the received electrical signals representing the second evoked compound action potential and the stored electrical signals corresponding to the first evoked compound action potential.

9. A non-transitory machine-readable medium including instructions, which when executed by a machine, cause the machine to:
   stimulate an external location on a patient's body to generate a first evoked compound action potential;
   receive electrical signals from a first location within the patient's body, the received electrical signals representing the first evoked compound action potential generated by the patient in response to stimulation of the external location;
   store the received electrical signals corresponding to the first evoked compound action potential in a memory;
   internally stimulate a location within the patient's body to generate a second evoked compound action potential;
   receive electrical signals from the first location, the received electrical signals representing the second evoked compound action potential generated by the patient in response to the internal stimulation;
   determine a difference between the received electrical signals representing the second evoked compound action potential to the stored electrical signals corresponding to the first evoked compound action potential; and
   adjust at least one electrical parameter of the internal stimulation to reduce the determined difference between the received electrical signals representing the second evoked compound action potential and the stored electrical signals corresponding to the first evoked compound action potential.

10. The non-transitory machine-readable medium of claim 9, further comprising instructions, which when executed by the machine, cause the machine to adjust at least one electrical parameter of the internal stimulation to provide neuromodulation to a dermatomal target stimulated by the stimulation of the external location.

11. The non-transitory machine-readable medium of claim 10, wherein adjusting at least one electrical parameter of the internal stimulation includes adjusting at least one of an amplitude, pulse width, or frequency.

12. The non-transitory machine-readable medium of claim 9, further comprising instructions, which when executed by the machine, cause the machine to use a matched filter to determine a difference between the received electrical signals representing the second evoked compound action potential and the stored electrical signals corresponding to the first evoked compound action potential.

13. A system comprising:
   recording circuitry configured to receive electrical signals from a first set of electrodes implanted within a patient, the first set of electrodes being configured to receive electrical signals representing evoked compound action potentials generated by the patient in response to stimulation of an external location on the patient's body and to record the received electrical signals in a memory;
   stimulation circuitry configured to apply electrical signals using a second set of electrodes implanted within the patient to provide neuromodulation to the patient; and
   control circuitry configured to:
   receive electrical signals representing evoked compound action potentials received at the first set of electrodes and generated by the patient in response to the electrical signals applied by the stimulation circuitry using the second set of electrodes, and to adjust one or more electrical parameters of the electrical signals applied by the stimulation circuitry using the second set of electrodes to increase a correlation between the electrical signals received by the control circuitry and the electrical signals recorded by the recording circuitry.

14. The system of claim 13 wherein the external location on the patient's body is a dermatomal target and wherein the control circuitry is configured to adjust the one or more electrical parameters of the electrical signals applied to the second set of electrodes to provide stimulation of the dermatomal target.

15. The system of claim 13 wherein the second set of electrodes includes electrodes on a paddle lead configured to provide spinal cord stimulation.

16. The system of claim 13 wherein the adjusted one or more electrical parameters include at least one of an amplitude, pulse width, or frequency.

17. The system of claim 13 wherein the first set of electrodes is located proximal to a dorsal root ganglia of the patient.

18. The system of claim 13 wherein the first set of electrodes is located in a neural foramen or epidural space of the patient.

19. The system of claim 13 wherein the control circuitry is configured to instruct the stimulation circuitry to adjust a charge delivered to the second set of electrodes to maintain measured electrical signals representing evoked compound action potentials at the first set of electrodes.

20. The system of claim 13 wherein the control circuitry is configured to use a matched filter to determine whether the adjusted one or more electrical parameters increases the correlation between the electrical signals received by the control circuitry and the electrical signals recorded by the recording circuitry.

* * * * *